United States Patent
Dernbach et al.

(10) Patent No.: US 7,057,080 B2
(45) Date of Patent: *Jun. 6, 2006

(54) COLOR INDEX OF MULTIVALENT ALCOHOLS BY HYDROGENATION

(75) Inventors: Matthias Dernbach, Dossenheim (DE); Christoph Sigwart, Schriesheim (DE); Michael Hesse, Worms (DE); Steffen Maas, Bubenheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 161 days.

This patent is subject to a terminal disclaimer.

(21) Appl. No.: 10/398,180

(22) PCT Filed: Oct. 11, 2001

(86) PCT No.: PCT/EP01/11763

§ 371 (c)(1),
(2), (4) Date: Apr. 2, 2003

(87) PCT Pub. No.: WO02/30858

PCT Pub. Date: Apr. 18, 2002

(65) Prior Publication Data

US 2004/0024265 A1     Feb. 5, 2004

(30) Foreign Application Priority Data

Oct. 13, 2000  (DE) .............................. 100 50 645

(51) Int. Cl.
*C07C 27/10*   (2006.01)

(52) U.S. Cl. ...................... 568/700; 568/853; 568/854

(58) Field of Classification Search ................ 568/700, 568/853, 854, 863
See application file for complete search history.

(56) References Cited

U.S. PATENT DOCUMENTS

| 5,603,835 A | 2/1997 | Cheung et al. |
| 6,187,971 B1 | 2/2001 | Kratz et al. |
| 6,586,642 B1 * | 7/2003 | Dernbach et al. ........... 568/854 |

FOREIGN PATENT DOCUMENTS

| DE | 1 768 259 | 10/1971 |
| EP | 601 571 | 6/1994 |
| GB | 1168216 | 10/1969 |
| SU | 125552 | 3/1959 |
| WO | 98/28253 | 7/1998 |
| WO | 99/20586 | 4/1999 |

OTHER PUBLICATIONS

Chem.Abst. vol. 55, No. 21, XP-002171005, 1987.

* cited by examiner

*Primary Examiner*—Johann Richter
*Assistant Examiner*—Chukwuma Nwaonicha
(74) *Attorney, Agent, or Firm*—Novak Druce Deluca & Quigg, LLP; Jason D. Voight

(57) ABSTRACT

A process is provided for improving the color number of polyhydric alcohols, especially trimethylolpropane, by catalytic hydrogenation, the polyhydric alcohol used in the hydrogenation having been purified by distillation following its preparation, wherein the hydrogenation is carried out in the presence of a macroporous supported heterogeneous catalyst containing, as the active metal, at least one metal of subgroups VII to X of the Periodic Table.

21 Claims, No Drawings

COLOR INDEX OF MULTIVALENT ALCOHOLS BY HYDROGENATION

The present invention relates to a process which affords polyhydric alcohols of low color number by hydrogenation.

Polyhydric alcohols are obtained on a large scale by condensing formaldehyde with higher CH-acidic aldehydes or with water and acrolein or 2-alkylacroleins. This reaction can be carried out according to two main procedural variants.

Firstly, there is the so-called Cannizzaro process, which is further subdivided into the inorganic and organic Cannizzaro processes. In the inorganic variant, excess formaldehyde is reacted with the appropriate alkanal in the presence of stoichiometric amounts of an inorganic base such as NaOH or $Ca(OH)_2$. In the second step, the dimethylolbutanal formed in the first step reacts with the excess formaldehyde in a disproportionation reaction to give trimethylolpropane and the formate of the base used, i.e. sodium or calcium formate. The production of these salts is a disadvantage because they are not easy to separate from the reaction product; in addition, one equivalent of formaldehyde is lost.

In the organic Cannizzaro process, a tertiary alkylamine is used in place of an inorganic base, affording higher yields than with an inorganic base. Trialkylammonium formate is obtained as an unwanted by-product, so here again one equivalent of formaldehyde is lost.

The disadvantages of the Cannizzaro process are avoided in the so-called hydrogenation process, where formaldehyde is reacted with the appropriate aldehyde in the presence of catalytic amounts of an amine, the result being that the reaction stops at the alkylolated aldehyde stage. After separation of the formaldehyde, the reaction mixture—which, in addition to said alkylolated aldehyde, also contains small amounts of the corresponding polyhydric alcohol and of acetals of the alcohols formed—is hydrogenated to give the desired polyhydric alcohol.

One particularly efficient process for the preparation of alcohols obtainable by condensing aldehydes with formaldehyde is described in WO 98/28253. This process affords high yields with the concomitant production of small amounts of coupling products. The procedure involves reacting the higher aldehyde with 2 to 8 times the amount of formaldehyde in the presence of a tertiary amine and separating the resulting reaction mixture into two solutions, one containing said fully methylolated alkanal and the other containing unreacted starting material. The latter solution is recycled into the reaction. The separation is effected by distillation or by simply separating the aqueous phase from the organic phase. The solution containing the product is subjected to a catalytic and/or thermal treatment to convert incompletely alkylolated alkanals to the desired fully methylolated compounds. By-product formed in this process is separated off by distillation and the resulting bottom product is subjected to catalytic hydrogenation to give the polyhydric alcohols.

Examples of important alcohols prepared by the processes described are neopentyl glycol, pentaerythritol, trimethylolethane, trimethylolbutane and, in particular, trimethylolpropane (TMP).

TMP has become widely used as a crosslinking agent for polyesters and polyurethanes. However, commercially available grades of TMP have a more or less pronounced coloration, probably caused by the presence of impurities. This coloration is not a problem for many uses, but there are also applications for which it is desirable to use TMP with as little color as possible. A variety of processes aimed at improving the color number of TMP are described in the literature.

U.S. Pat. No. 3,097,245 describes a process for the preparation of trimethylolpropane with an APHA color number of between 50 and 200. This color number is achieved by observing specific reaction conditions in respect of temperature, reaction time, pH and concentration of the starting compounds. The reaction is also followed by treatment of the resulting solution with an ion exchange resin.

U.S. Pat. No. 5,603,835 discloses a process for the preparation of TMP with APHA color numbers of <100. These are achieved by means of an extractive aftertreatment of the resulting crude TMP solutions with an ether or an ester. The TMP solutions used generally originate from the Cannizzaro process.

Both the processes described above have the disadvantage of being relatively expensive because specific conditions have to be observed precisely and it is necessary to add an ion exchange resin or introduce at least one solvent.

The literature only contains a small amount of information on the hydrogenation of products formed by condensing formaldehyde with higher aldehydes.

DE-A-17 68 259 discloses a process for the processing of the by-products formed when reacting formaldehyde with higher aldehydes to give polyhydric alcohols. The process consists in separating these by-products from the main product and then hydrogenating them to give comparatively large amounts of mainly aliphatic alcohols.

WO 99/20586 describes a process for the preparation of trimethylolpropane with a low reacted color (color number according to standardized boiling tests). The crude trimethylolpropane prepared by the Cannizzaro reaction is heated with a water/solvent mixture to form a single-phase solution. This is then cooled and separates into at least 2 phases. The trimethylolpropane is recovered from the aqueous phase by a two-stage distillation and normally has an acid wash color of 1 to 1.5 Gardner (GU) and a phthalic anhydride color number of 1 GU. The disadvantage of this process is the loss of more than 10% of the trimethylolpropane, which dissolves in the organic phase. Moreover, the process is technically expensive and an improvement in the natural color number is not reported.

The hydrogenation process described in SU-A 125 552 is used to purify TMP obtained by the Cannizzaro process, said TMP being either a crude material in the form of an aqueous solution containing approx. 30% of TMP, or a purified material containing approx. 80% of TMP, from which water and formates have been removed. Hydrogenation on nickel, zinc, molybdenum and copper catalysts affords pure TMP with a content of approx. 98% after distillation. The pressures used are 1 to 250 bar, preferably 10 to 200 bar, and the temperatures are 20 to 200° C., preferably 100 to 150° C. The TMP obtained is said to be colorless, although no color number is mentioned.

It has been found, however, that the improvements in color number obtainable by this process are often inadequate for many purposes.

It is therefore an object of the present invention to provide a process which makes it possible to obtain polyhydric alcohols, especially TMP, with a low color number. APHA color numbers of <20 should be achievable by this process.

We have found that this object is achieved by a process for improving the color number of polyhydric alcohols by catalytic hydrogenation, the polyhydric alcohol used in the hydrogenation having been purified by distillation following its preparation, wherein the hydrogenation is carried out in the presence of a macroporous supported heterogeneous catalyst containing, as the active metal, at least one metal of subgroups VII to X of the Periodic Table.

It has been established that by using already distilled polyhydric alcohol and carrying out the hydrogenation in the presence of a macroporous supported heterogeneous catalyst containing, as the active metal, at least one metal of subgroups VII to X of the Periodic Table, an improvement in color number can be achieved which is far greater than that achieved using an alcohol which has not been purified beforehand by distillation. Good results have been obtained with solutions containing >95% of alcohol.

If TMP is used in the hydrogenation, particularly good results can be achieved by using TMP solutions with a content of >98%.

The process according to the invention can be used to improve the color number of polyhydric alcohols, especially TMP, of any origin. Batches originating from the organic or inorganic Cannizzaro process can be used in the hydrogenation according to the present invention for improving the color number in just the same way as can alcohols originating from the hydrogenation process, although it is preferred to use alcohols originating from the hydrogenation process. The only important point is that the alcohol has been purified beforehand and is of a purity which is within the above-mentioned range and hence allows the color number to be improved by means of the process according to the invention.

The hydrogenation according to the invention is applicable to any polyhydric alcohols which can be prepared by condensing formaldehyde with higher aldehydes, in the presence of catalytic amounts of trialkylamine, and then hydrogenating the products. Practically any alkanals with an acidic hydrogen atom in the α-position to the carbonyl group are suitable higher aldehydes. Starting materials which can be used are aliphatic aldehydes having from 2 to 24 C atoms which can be linear or branched or can also contain alicyclic groups. Other suitable starting materials are araliphatic aldehydes, provided that they contain a methylene group in the α-position to the carbonyl group. In general, aralkyl aldehydes having from 8 to 24 C atoms, preferably from 8 to 12 C atoms, for example phenylacetaldehyde, are used as starting materials. Aliphatic aldehydes having from 2 to 12 C atoms are preferred, examples being 3-ethyl-, 3-n-propyl-, 3-isopropyl-, 3-n-butyl-, 3-isobutyl-, 3-sec-butyl- and 3-tert-butylbutanal and the corresponding n-pentanals, n-hexanals and n-heptanals; 4-ethyl-, 4-n-propyl-, 4-isopropyl-, 4-n-butyl-, 4-isobutyl-, 4-sec-butyl- and 4-tert-butylpentanals, -n-hexanals and -n-heptanals; 5-ethyl-, 5-n-propyl-, 5-isopropyl-, 5-n-butyl-, 5-isobutyl-, 5-sec-butyl- and 5-tert-butyl-n-hexanals and -n-heptanals; 3-methylhexanal and 3-methylheptanal; 4-methylpentanal, 4-methylheptanal, 5-methylhexanal and 5-methylheptanal; 3,3,5-trimethyl-n-pentyl-, 3,3-diethylpentyl-, 4,4-diethylpentyl-, 3,3-dimethyl-n-butyl-, 3,3-dimethyl-n-pentyl-, 5,5-dimethylheptyl-, 3,3-dimethylheptyl-, 3,3,4-trimethylpentyl-, 3,4-dimethylheptyl-, 3,5-dimethylheptyl-, 4,4-dimethylheptyl-, 3,3-diethylhexyl-, 4,4-dimethylhexyl-, 4,5-dimethylhexyl-, 3,4-dimethylhexyl-, 3,5-dimethylhexyl-, 3,3-dimethylhexyl-, 3,4-diethylhexyl-, 3-methyl-4-ethylpentyl-, 3-methyl-4-ethylhexyl-, 3,3,4-trimethylpentyl-, 3,4,4-trimethylpentyl-, 3,3,4-trimethylhexyl-, 3,4,4-trimethylhexyl- and 3,3,4,4-tetramethylpentylaldehyde; $C_2$ to $C_{12}$ n-alkanals are particularly preferred.

Particularly preferred polyhydric alcohols within the framework of the present invention are trimethylolethane, trimethylolpropane, trimethylolbutane, neopentyl glycol and pentaerythritol, trimethylolpropane being very particularly preferred.

If the color number of TMP is to be improved by the process according to the invention, a TMP of high purity (>98%) prepared by the hydrogenation process can be obtained for example by the process described in German patent application DE 19963435.1 entitled "Verfahren zur Reinigung von durch Hydrierung hergestelltem Trimethylolpropan durch kontinuierliche Destillation" (Applicant: BASF AG). In this process, the crude product obtained after hydrogenation is first subjected to dehydration, in which water and other low-boiling components, such as methanol, trialkylamine or trialkylammonium formate, are separated off by distillation. This distillation can be carried out at pressures of <400 mbar, preferably of 20 to 200 mbar, at bottom temperatures of <200° C. and for short residence times so that the trialkylammonium formate produced reacts to only a small extent with TMP to give TMP formates and trialkylamine. It is also possible to carry out the distillation at pressures of >200 mbar, preferably of >400 mbar, at bottom temperatures of >140° C. and for short residence times so that at least the bulk of the TMP reacts with trialkylammonium formate to give TMP formates and trialkylamine.

The high-boiling components are then separated off in the next step. This is carried out by distilling from the bottom product, at 210 to 250° C., those components which are volatile at these temperatures. The high-boiling components thus remain in the bottom product. The low-boiling TMP-rich fraction obtained is then worked up by distillation (first distillative purification) to separate off unwanted low-boiling components. The pure product obtained can be subjected to a second distillative purification to give a particularly clean product.

The content of said German patent application is an important and integral part of the present invention and is included in the present patent application by reference.

The process described in this patent application can have further variants. Thus it is possible, for example, to react the TMP formate produced with a suitable amine, preferably a dialkylamine, to give TMP and dialkylformamide. Such a process is described in German patent application DE 19963444.0 entitled "Verfahren zur Umwandlung von bei der Trimethylolalkan-Herstellung gebildeten Trimethylolalkanformiat" (Applicant: BASF AG).

A further possibility is to increase the yield by decomposing the high-boiling components through the addition of acid to give TMP and other products. Such a process is described in German patent application DE 19963437.8 entitled "Verfahren zur Zersetzung von bei der Synthese mehrwertiger Alkohole gebildeter Nebenprodukte" (Applicant: BASF AG).

Good results have been obtainable with a TMP, purified by distillation in this or another way, which has color numbers of 1 to 500 APHA, preferably of 15 to 120 APHA.

The hydrogenation according to the present invention makes it possible to prepare polyhydric alcohols with APHA color numbers of <10, especially TMP with a color number of 1 APHA.

The hydrogenation according to the invention is carried out at temperatures of 20 to 300° C., preferably of 100 to 180° C., the applied pressures being 1 to 350 bar, preferably 1 to 100 bar. The residence times used in this process are 5 minutes to 20 hours, preferably 10 minutes to 8 hours. It is possible to choose a batch procedure, which is preferably carried out in a stirred tank. Another equally good possibility is to carry out the hydrogenation continuously, preferably in tubular reactors by the liquid phase or trickle method.

The macroporous hydrogenation catalysts used in the process according to the invention are macroporous supported heterogeneous catalysts containing, as the active metal, at least one metal of subgroups VII to X of the Periodic Table. In principle, the macroporous heterogeneous catalyst can contain any metals of subgroups VII to X of the Periodic Table of the Elements as the active metal. The active metals used are preferably palladium, ruthenium, rhenium, nickel, iron and cobalt or a mixture of two or more active metals; palladium is used in particular as the active metal.

Within the framework of the present invention, the term "macroporous" is used as defined in Pure Appl. Chem., 46, p. 79 (1976), namely as pores with diameters larger than 50 nm. The content of macropores with a diameter of more than 100 nm in the heterogeneous catalyst used according to the invention, based on the total pores, i.e. the macroporosity of the heterogeneous catalyst, is greater than 10% by volume, preferably greater than 20% by volume and particularly preferably 25 to 90% by volume, based in each case on the total pores.

The active metal content is generally 0.01 to 10% by weight, preferably 0.05 to 5% by weight and particularly preferably 0.1 to 3% by weight, based on the total weight of the catalyst.

The total surface area of metal on the macroporous supported catalyst used according to the invention is preferably 0.01 to 10 $m^2/g$, particularly preferably about 0.05 to 5 $m^2/g$ and very particularly preferably about 0.05 to 3 $m^2/g$ of catalyst. The surface area of metal is determined by means of chemisorption methods described by J. LeMaitre et al. in "Characterization of Heterogeneous Catalysts", published by Francis Delanney, D, New York 1984, pp. 310–324.

The macroporous heterogeneous catalysts used according to the invention can be prepared industrially by various methods known per se, for example by the application of at least one metal of subgroups VII to X of the Periodic Table of the Elements to a suitable macroporous support.

The application can be effected by impregnating the support with aqueous metal salt solutions, e.g. aqueous palladium salt solutions, by spraying appropriate metal salt solutions onto the support or by other suitable methods. Suitable salts of metals of subgroups VII to X of the Periodic Table of the Elements are nitrates, nitrosylnitrates, halides, carbonates, carboxylates, acetylacetonates, chloro complexes, nitro complexes or amine complexes of said metals, nitrates and nitrosylnitrates being preferred. In the case of catalysts containing several metals of subgroups VII to X of the Periodic Table, the metal salts or solutions thereof can be applied simultaneously or successively.

The supports coated or impregnated with metal salt solutions are then dried, preferably at temperatures of between 100° C. and 150° C., and optionally calcined at temperatures of between 200° C. and 600° C., preferably of 350° C. to 450° C. In the case of separate impregnations, the catalyst is dried and optionally calcined after each impregnation step, as described above. The operator is free to choose the sequence in which the active components are impregnated.

The coated, dried and optionally calcined supports are then activated by treatment in a gas stream containing free hydrogen, at temperatures of 30° C. to 600° C., preferably of between 150° C. and 450° C. The gas stream is preferably composed of 50 to 100% by volume of $H_2$ and 0 to 50% by volume of $N_2$.

The support materials which can be employed to prepare the catalysts used according to the invention are those which are macroporous, have a mean pore diameter of at least 50 nm, preferably of at least 100 nm and particularly preferably of 500 nm, and whose BET surface area is at most about 300 $m^2/g$, preferably about 15 $m^2/g$, particularly preferably about 10 $m^2/g$, especially about 5 $m^2/g$ and very particularly preferably at most 3 $m^2/g$.

The surface area of the support is determined by $N_2$ adsorption using the BET method, especially according to DIN 66131. The pore diameter and pore distribution are determined by Hg porosimetry, especially according to DIN 66133.

Although it is possible in principle to use any of the support materials known for the preparation of catalysts, i.e. those with the macroporosity defined above, it is preferred to use activated carbon, silicon carbide, silicon oxide, mullite, cordierite, aluminum oxide, titanium oxide, zirconium oxide, magnesium oxide, zinc oxide or mixtures thereof, aluminum oxide, zirconium dioxide and mullite being particularly preferred and aluminum oxide being very particularly preferred.

Furthermore, the macroporous heterogeneous catalysts used according to the invention can be prepared industrially by the process known from EP-A-653 243, in which the active metal and the macropores are introduced in one step. In the process known from EP-A-653 243, the macroporous heterogeneous catalysts used according to the invention are prepared by dissolving a water-soluble salt of a metal of subgroups VII to X of the Periodic Table of the Elements in an organic solvent, treating the resulting solution with an organic polymer capable of binding at least ten times its own weight of water, then mixing the polymer with a catalyst support material and shaping, drying and calcining the mass obtained.

Suitable water-soluble salts of a metal of subgroups VII to X of the Periodic Table of the Elements are preferably nitrates, nitrosylnitrates, halides, carbonates, carboxylates, acetylacetonates, chloro complexes, nitro complexes or amine complexes of said metals, nitrates and nitrosylnitrates being particularly preferred. Preferred solvents are water-miscible solvents such as alcohols, ethers and amines. Alcohols which may be mentioned in particular are $C_1$–$C_4$-alcohols such as methanol, ethanol, isopropanol and n-butanol; a suitable ether is e.g. tetrahydrofuran. Examples of suitable amines are ammonia and monoamines such as diethylamine, methylamine, triethylamine, ethylamine, propylamine and butylamine.

The organic polymers used are preferably crosslinked polymers of acrylic acid, acrylic acid/acrylamide and acrylamide, particular preference being given to partially neutralized sodium polyacrylates which are weakly crosslinked. Examples of suitable chemical crosslinking agents are diols such as ethylene glycol and polyethylene glycol, polyols, diamines and dienes in amounts of 0.1 to 5% by weight, based on the polymer.

Preferred support materials are activated carbon, silicon carbide, aluminum oxide, titanium oxide, mullite, cordierite, zirconium oxide, magnesium oxide, zinc oxide or mixtures thereof, aluminum oxide, zirconium dioxide and mullite being particularly preferred and aluminum oxide being very particularly preferred.

Further details on the preparation of the macroporous catalysts used according to the invention by introducing the active metal and the macropores in one step can be found in EP-A-653 243, the relevant content of which is fully included in the present patent application by reference.

Furthermore, the macroporous catalysts used according to the invention can be prepared industrially using pore-forming agents by the process known from EP-A-842 699. Any water-miscible polymers can be used as pore-forming agents provided they have a molecular weight of more than about 6000 to 500,000 g/mol. Their molecular weight is preferably about 10,000 to about 200,000 g/mol, particularly preferably about 13,000 to about 150,000 g/mol and very particularly preferably about 13,000 to about 50,000 g/mol. Examples of polymers which can be used include polyvinyl chloride, copolymers of an olefin with polar comonomers, e.g. ethylene or propylene with polyvinyl chloride, polyvinylidene chloride copolymers, ABS resins, polyethylene copolymers with vinyl acetate, alkyl acrylates or acrylic acid, chlorinated polyethylenes, chlorosulfonated polyethylenes, thermoplastic polyurethanes, polyamides such as nylon-5, nylon-12, nylon-6,6, nylon-6,10 and nylon-11, fluorine-containing resins such as FEP, polyvinylidene fluoride and polychlorotrifluoroethylene, acrylonitrile/(meth)acrylate copolymers such as methacrylonitrile/styrene copolymers, polyalkyl (meth)acrylates, cellulose acetate, cellulose acetate-butyrate, polycarbonates, polysulfones, polyphenylene oxide, polyesters such as polybutylene terephthalate, and polyvinyl alcohol, polyvinyl alcohol being particularly preferred.

The first step in the preparation of the macroporous catalysts used according to the invention is to prepare an aluminum alloy of aluminum and the active metal of subgroups VII to X of the Periodic Table of the Elements, this being done in known manner by the process known from DE 2 159 736.

This is followed, according to EP-A-0 842 699, by the preparation of a kneading compound from this alloy, a molding agent, water and the pore-forming agent, shaping of this kneading compound into moldings, calcination of the molding and, finally, treatment of the calcined molding with an alkali metal hydroxide.

Further details on this industrial process for the preparation of the macroporous catalysts used according to the invention can be found in EP-A-842 699, the relevant content of which is fully included in the present patent application by reference.

The macroporous catalysts used according to the invention are preferably prepared by impregnating a suitable macroporous support with at least one metal of subgroups VII to X of the Periodic Table of the Elements.

If desired, the macroporous catalysts used according to the invention can additionally be doped with bases in order to prevent recleavage of the polymer during the hydrogenation, especially at high hydrogenation temperatures. Examples of suitable bases are basic oxides such as alkali metal or alkaline earth metal oxides, e.g. sodium oxides, potassium oxides, calcium oxides and barium oxides, sodium oxides being particularly preferred. These oxides, or their precursors such as the corresponding hydroxides, carbonates or hydroxycarbonates, can be applied to the catalyst for example by impregnation in supernatant solution or spray impregnation, or during the structural agglomeration of the support, in concentrations of 0.05–5%, based on the weight of the catalyst. If appropriate, this is followed by tempering to thermally decompose the precursors.

Before being used in the hydrogenation, the macroporous catalysts used according to the invention can be reduced with hydrogen.

The macroporous catalysts usable according to the invention can be employed in the process according to the invention in the form of powder, for example when carrying out the process by the suspension method, or expediently as moldings, e.g. in the form of strands, cylinders, spheres, rings or grit, especially when the catalyst is in a fixed bed arrangement.

The hydrogenation according to the invention using the macroporous heterogeneous catalysts described above is preferably carried out in a fixed bed and it has proved advantageous to perform the reaction in a primary reactor in a single pass. Equally good results have been obtained by carrying out the hydrogenation in a primary reactor with a secondary reactor downstream, the primary reactor operating as a loop reactor and the secondary reactor operating as a single-pass reactor. The liquid phase or trickle method can be chosen in each case. The hydrogenation is preferably carried out in a fixed bed in a single pass by the liquid phase method.

The hydrogenation according to the invention of TMP purified beforehand by distillation can be carried out with or without the addition of another solvent. If such a solvent is used, it is added in concentrations such that the solutions employed in the hydrogenation have a TMP content of 5 to 95% by weight. The solvents used here are preferably low-boiling organic solvents such as alcohols, ethers, hydrocarbons or esters. Preferred solvents include methanol, ethanol, n-propanol, i-propanol, butanol, diethyl ether, methyl tert-butyl ether, dioxane, tetrahydrofuran and ethyl acetate. Particularly preferred solvents are methanol and tetrahydrofuran. If the hydrogenation according to the invention is carried out in the presence of an additional solvent, a separating unit is included downstream of the hydrogenation unit in order to separate the solvent from the TMP obtained in this way. Examples of conventional separating units are distillation columns, film evaporators and, preferably, falling film evaporators.

The process according to the invention will now be illustrated with the aid of the following Examples. The TMP used in all the Examples had been prepared as follows:

An apparatus consisting of two heatable stirred tanks with an overall capacity of 72 l, interconnected by overflow tubes, was charged continuously with fresh aqueous formaldehyde solution (4300 g/h) in the form of a 40% aqueous solution, and n-butyraldehyde (1800 g/h), and with fresh trimethylamine as catalyst (130 g/h) in the form of a 45% aqueous solution. The reactors were heated to a constant temperature of 40° C.

The discharge was passed directly into the top of a falling film evaporator with attached column, where it was separated by distillation under atmospheric pressure into a low-boiling top product, essentially containing n-butyraldehyde, ethylacrolein, formaldehyde, water and trimethylamine, and a high-boiling bottom product.

The top product was continuously condensed and recycled into the reactors described above.

The high-boiling bottom product from the evaporator (approx. 33.5 kg/h) was treated continuously with fresh trimethylamine catalyst (50 g/h) in the form of a 45% aqueous solution, and transferred to a heatable, packed tubular reactor with an empty volume of 12 l. The reactor was heated to a constant temperature of 40° C.

The discharge from the secondary reactor was passed continuously into the top of another distillation device for separation of the formaldehyde (superheated steam at 11 bar), where it was separated by distillation into a low-boiling top product, essentially containing ethylacrolein, formaldehyde, water and trimethylamine, and a high-boiling bottom product. The low-boiling top product (27 kg/h) was continuously condensed and recycled into the first stirred tank, while the high-boiling bottom product was collected.

In addition to water, the resulting bottom product contained essentially dimethylolbutyraldehyde, formaldehyde and traces of monomethylolbutyraldehyde. This bottom product was then subjected to continuous hydrogenation. This was done by hydrogenating the reaction solution at 90 bar and 115° C. in a primary reactor by the loop/trickle method and in a downstream secondary reactor by the loop method. The catalyst was prepared analogously to Example J of DE 19809418 and contained 42% by weight of CuO, 16% by weight of Cu and 46% of $TiO_2$. The apparatus used consisted of a heated primary reactor with a length of 10 m (internal diameter: 27 mm) and a heated secondary reactor with a length of 5.3 m (internal diameter: 25 mm). The loop throughput was 25 l/h of liquid and the reactor feed was adjusted to 4 kg/h, corresponding to a hydrogenation discharge of 4 kg/h.

After hydrogenation, the TMP was withdrawn from the bottom of the column and worked up by distillation according to the method described in Examples 2 and 3 of German patent application DE 19963435.1 entitled "Verfahren zur Reinigung von durch Hydrierung hergestelltem Trimethylolpropan durch kontinuierliche Destillation" (Applicant: BASF AG). The TMP used in some of the Examples was taken from the first distillative purification column (grade A). The TMP used in other Examples originated from the second distillative purification (grade B).

The TMP already hydrogenated by the process according to the invention can be subjected to a further hydrogenation in order to improve the color number, preferably using a different catalyst.

The indicated APHA color numbers were measured with a LICO 200 instrument from the company Dr. Lange. The TMP samples were measured in the pure form in the melt at 100° C.

EXAMPLES

Preparation of Catalyst A 119 g of aqueous palladium nitrate solution (12.6% by weight of palladium) were diluted with 1868 ml of water and sprayed onto 5985 g of a macroporous aluminum support in strand form (4 mm strands, alpha-$Al_2O_3$, BET surface area 6.5 $m^2/g$). Drying took place at 120° C. in a stationary layer and was followed by tempering for 2 h at 500° C. Catalyst A contained 0.21% by weight of palladium and had a macropore content of about 61%.

Example 1

A grade A TMP was hydrogenated which had a color number of 105 APHA and a TMP content of 99.0%. The hydrogenation was carried out in a tubular reactor by the liquid phase method on 100 ml of catalyst A. The temperature was 140° C., the pressure was 80 bar and the feed was adjusted to 0.6 ml/min. The TMP obtained after hydrogenation and passage through a filter had an APHA color number of 17.

Example 2

A grade A TMP was hydrogenated which had a color number of 62 APHA and a TMP content of 89.9%. The hydrogenation was carried out analogously to Example 1 in a tubular reactor by the liquid phase method on 100 ml of catalyst A. The temperature was again 140° C. The pressure was adjusted to 20 bar and the feed to 0.3 ml/min. The TMP obtained after hydrogenation and passage through a filter had an APHA color number of 23.

Example 3

The hydrogenation was carried out analogously to Example 2. A grade B TMP was hydrogenated which had a color number of 18 APHA and a TMP content of 89.9%. The pressure was adjusted to 60 bar and the feed to 0.3 ml/min. The TMP obtained after hydrogenation and passage through a filter had an APHA color number of 1.

To exclude the possibility of the filtration not improving the color number, the starting material was passed through the filter and the color number was measured. It was identical to the color number of the educt.

We claim:

1. A process for improving the color number of polyhydric alcohols, especially trimethylolpropane, by catalytic hydrogenation, the polyhydric alcohol used in the hydrogenation having been purified by distillation following its preparation, wherein the hydrogenation is carried out in the presence of a macroporous supported heterogeneous catalyst containing, as the active metal, at least one metal of subgroups VII to X of the Periodic Table.

2. A process as claimed in claim 1 wherein the polyhydric alcohol used in the hydrogenation has a product content of >95%.

3. A process as claimed in claim 1 wherein the macroporous heterogeneous catalyst contains, as active metals, palladium, ruthenium, rhenium, nickel, iron and/or cobalt or a mixture of two or more of these active metals.

4. A process as claimed in claim 3 wherein the macroporosity of the heterogeneous catalyst is greater than 10% by volume.

5. A process as claimed in claim 4 wherein aluminum oxide and/or zirconium dioxide are used as the support material.

6. A process as claimed in claim 5 wherein the heterogeneous catalyst has a surface area of metal of 0.01 to 10 $m^2/g$.

7. A process as claimed in claim 6 wherein the heterogeneous catalyst has a BET surface area of 0.1 to 300 $m^2/g$.

8. A process as claimed in claim 7 wherein the heterogeneous catalyst has an active metal content of 0.01 to 10% by weight.

9. A process as claimed in claim 1 wherein the hydrogenation is carried out at temperatures of 20 to 300° C.

10. A process as claimed in claim 1 wherein the hydrogenation is carried out at pressures of 1 to 350 bar.

11. A process as claimed in claim 1 wherein the residence times of the TMP in the reactor are from 5 min to 20 hours.

12. A process as claimed in claim 1 wherein the hydrogenation is carried out batchwise.

13. A process as claimed in claim 1 wherein the hydrogenation of trimethylolpropane is carried out without the addition of a solvent or with the addition of 5 to 95% by weight of a solvent.

14. A process as claimed in claim 2 wherein the polyhydric alcohol is a trimethylolpropane which has a product content of >98%.

15. A process as claimed in claim 1 wherein the hydrogenation is carried out at temperatures of 100 to 180° C.

16. A process as claimed in claim 1 wherein the hydrogenation is carried out at pressures of 1 to 100 bar.

17. A process as claimed in claim 1 wherein the hydrogenation is carried out at pressures of 1 to 50 bar.

18. A process as claimed in claim 1 wherein the residence times of the TMP in the reactor are from 10 min to 8 hours.

19. A process as claimed in claim 12 wherein the hydrogenation is carried out in a stirred tank.

20. A process as claimed in claim 1 wherein the hydrogenation is carried out continuously.

21. A process as claimed in claim 20 wherein the hydrogenation is carried out in tubular reactors by means of a liquid phase or trickle method.

* * * * *